United States Patent [19]
Jones

[11] Patent Number: 5,541,106
[45] Date of Patent: Jul. 30, 1996

[54] CELL MATRIX STIMULATED ATTACHMENT AND HEMIDESMOSOME ASSEMBLY

[75] Inventor: Jonathan C. R. Jones, Chicago, Ill.

[73] Assignee: Desmos, Inc., San Diego, Calif.

[21] Appl. No.: 324,367

[22] Filed: Oct. 14, 1994

Related U.S. Application Data

[63] Continuation of Ser. No. 42,727, Apr. 5, 1993, abandoned.

[51] Int. Cl.$^6$ .............................. C12N 5/00; C12P 21/04; A61F 2/02; A61F 2/10
[52] U.S. Cl. ................ 435/240.243; 435/240.2; 435/240.23; 435/70.1; 435/70.3; 623/11; 623/15
[58] Field of Search .................. 435/240.2, 240.21, 435/240.23, 230.243, 70.1, 70.3; 623/11, 15

[56] References Cited

U.S. PATENT DOCUMENTS

| | | | |
|---|---|---|---|
| 5,007,925 | 4/1991 | Tsilibary et al. | 623/1 |
| 5,422,264 | 6/1995 | Luaranta et al. | 435/240.2 |

FOREIGN PATENT DOCUMENTS

| | | |
|---|---|---|
| WO92/17498 | 10/1992 | WIPO . |
| WO94/05316 | 3/1994 | WIPO . |

OTHER PUBLICATIONS

M. Langhofer and J. C. R. Jones "Matrix Signals Transduced by the α684 Interrim Complex" Mol. Biol. Cell (1992) 3 Suppl., Abstract 550, p. 95A.

J. C. R. Jones et al. "α6β4 Integrins: Their Role in the Assembly of the Hemidesmosome (YD) and in Signal Transduction" J. Cell. Biochem (1992) Suppl. 16F, Abstract X007, p. 142.

J. C. R. Jones "Hemisdesmosomes, Collagen VII, and Intermediate Filaments in Basal Cell Carcinoma" Journal of Investigative Dermatology (1989) vol. 93, No. 5, pp. 662–671.

P. Rousselle et al. "Kalinin is More Efficient Than Laminin in Promoting Adhesion of Primary Keratinocytes and Some Other Epithelial Cells and Has a Different Requirement for Integrin Receptors" Jour. of Cell Bio. (1994) vol. 125, pp. 205–214.

P. Rousselle et al. "Kalinin: An Epithelium–Specific Basement Membrane Adhesion Molecule that is a Component of Anchoring Filaments" Jour. of Cell Bio. (1991) vol. 114, pp. 567–576.

Jones et al., *Current Opinion in Cell Biology* (1991), "Intermediate Filament–Plasma Membrane Interactions", 3:127–132.

Schwarz et al., *Annu. Rev. Cell Biol.* (1990), "Desmosomes and Hemidesmosomes: Constitutive Molecular Components", 6:461–491.

Chapman, et al., Abnormal Expression of Hemidesmosome–Like Structures by Junctional Epidermolysis Bullosa Keratinocytes in Vitro, *British Journal of Dermatology* 123:137, 1990.

Giudice, et al., Identification of Two Collagen Domains Within the Bullous Pemphigoid Autoantigen, BP–180, *J. Clin. Invest.* 87:734, 1991.

Hieda, et la., Identification of a New Hemidesmosomal Protein, HD1: A Major, High Molecular Mass Component of Isolated Hemidesmosomes, *The Journal of Cell Biology* 116:1497, 1992.

Hopkinson, et al., Cytoplasmic Domain of the 180kD Bullous Pemphigoid Antigen, A Hemidesmosomal Component: Molecular and Cell Biologic Characterization, *The Journal of Investigative Dermatology* 99:264, 1992.

Izumi, et al., In Vitro Induction of Ornithine Decarboxylase in Urinary Bladder Carcinoma Cells, *Cancer Research* 41:405, 1981.

Kurpakus, et al., Surface Relocation of Alpha$_6$Beta$_4$ Integrins and Assembly of Hemidesmosomes in an in Vitro Model of Wound Healing, *The Journal of Cell Biology* 115:1737, 1991.

Staehelin, Structure and Function of Intercellular Junctions, *Department of Molecular, Cellular and Developmental Biology, University of Colorado, Boulder, Colorado* pp. 191–283.

Stepp, et al., $\alpha_6\beta_4$ Integrin Heterodimer is a Component of Hemidesmosomes *Proc. Natl. Acad. Sci. USA* 87:8970, 1990.

Sonneberg, et al., Integrin α6/β4 Complex is Located in Hemidesmosomes, Suggesting a Major Roles in Epidermal Cell–Basement Membrane Adhesion, *The Journal of Cell Biology* 113:907, 1991.

Langhofer et al., J. of Cell Science, vol. 105 (1993) pp. 753–764.

Riddelle et al., J. Cell Biol., 112(1) (Jan. 1991) pp. 159–168.

Riddelle et al. Mol. Biol. Cell 3 (Suppl) 1992, p. 70A.

Wucha et al. Proc. Natl. Acad. Sci (USA) 79(10) pp. 3213–3217 (1982) Abstract only.

Martin et al., Growth & Differentiation of Cells in Defined Environment, pp. 85–87 (1985).

*Primary Examiner*—Michael G. Wityshyn
*Assistant Examiner*—Susan M. Dadio
*Attorney, Agent, or Firm*—Knobbe, Martens, Olson & Bear

[57] ABSTRACT

A method for growing epithelial cells in vitro is described. The matrix secreted by 804G rat bladder carcinoma cells is able to stimulate cell attachment and hemidesmosome formation in cells grown on the matrix. Human epithelial cells grown on the 804G matrix are able to produce normal hemidesmosomes and attach to their growing substrate. Shaped articles coated with the matrix are also disclosed.

23 Claims, No Drawings

CELL MATRIX STIMULATED ATTACHMENT AND HEMIDESMOSOME ASSEMBLY

This application is a continuation of application Ser. No. 08/042,727, filed Apr. 5, 1993 now abandoned.

BACKGROUND

When organs of the body are formed, they develop in neatly organized arrays. Often, cell groups of one kind are separated from cells of another kind by flat strips of connective tissue called basement membranes. In skin, for instance, the superficial layer of epidermal cells adheres to the underlying basement membrane. This skin basement membrane acts as a barrier between the epidermal cells on the outside, and the dermal cells underneath. A similar arrangement of cells occurs in the lining of the gut.

Basement membranes have been implicated in the growth, attachment, migration, repair, and differentiation of their overlying cell populations. Three layers have been defined in basement membranes: a) the Lamina lucida, an electronmicroscopically clear region that resides in close approximation to the overlying cells; b) the lamina densa, an electron dense region of 20–300 nm in width; and c) the sublamina densa that contains anchoring fibrils, microfibrillar bundles and collagen fibers.

Many different types of compounds have now been localized to the basement membrane. Some of these compounds are laminin, collagen IV and heparin sulfate proteoglycans (Verrando et al. *Exp. Cell Res.* (1987); 170: 116–128). In addition, specific basement membranes include other biologically active components, such as nidogen and entactin.

The principal cell adhesion receptor that epidermal cells use to attach to the basement membrane is called α6β4. This transmembrane receptor is formed by a combination of two protein moieties α6 and β4. The α6 and β4 proteins are derived from different genes that have been found to be part of the integrin family.

Integrins are versatile family cell adhesion receptors. So far, approximately twenty members have been discovered in the integrin family. These molecules are involved in many types of cell adhesion phenomena in the body. Integrins are signalling molecules that can translate environmental cues into cellular instructions. Further, integrins can also transmit signals in the reverse direction, from the cell interior to the exterior. This has been illustrated in non-adherent cells, such as lymphocytes.

Stimulation of the T-cell antigen receptor, or of the CD3 complex, augments the affinity of certain integrins for their respective ligands. Unfortunately, in adherent cells, changes in the affinities of integrins have been more difficult to demonstrate. However, affinity modulation of one integrin in differentiating epidermal keratinocytes has been described by Adams et al. (Cell (1990); 63:425–435). For this reason, modifications of cell status initiated by activation or differentiation of other receptors may influence integrin affinity, and ultimately, the adhesive behavior of cells. Further, as a consequence of adhering to a surface, an integrin may actively contribute to modifying cell shape or migration.

Many epithelial cells interact with the underlying extracellular matrix via a junction called the hemidesmosome (Staehelin, 1974). Over the last few years there has been considerable progress in the biochemical characterization of this junction (Schwartz, et al., 1990). The hemidesmosome, with its associated structures such as intermediate filaments and anchoring fibrils, forms an adhesion complex. Disruptions of the epithelial-connective tissue interaction are often accompanied by disruption of the hemidesmosome complex. For example, in certain blistering skin diseases such as junctional epidermolysis bullosa where epithelial cell-connective tissue interaction is abnormal, it has been proposed that there is a biochemical modification in or loss of a basement membrane zone-associated component of the hemidesmosome.

Two high molecular weight intracellular components of the hemidesmosome have been identified and characterized with the aid of antisera from patients suffering from bullous pemphigoid. This autoimmune disease results in a disruption of the interactions between epithelial cells and connective tissue simultaneously with loss of hemidesmosome integrity (Chapman et al. *Br. J. Dermatol* (1990); 123:137–144). Accordingly, it was discovered that bullous pemphigoid patients were producing antibodies against hemidesmosome components. Two hemidesmosome related bullous pemphigoid (BP) antigens have been previously described (Klatte, et al., 1989).

One BP antigen is a 230 kD polypeptide that may act as an anchor for cytoskeleton elements in the hemidesmosomal plaque (Jones and Green, 1991). A second BP antigen is a type II membrane protein that possesses a collagen-like extracellular domain (Giudice, et al., 1991; Hopkinson, et al., 1992). In addition, it has been demonstrated that the interaction of the hemidesmosome with the underlying connective tissue involves the $\alpha_6\beta_4$ integrin heterodimer (Stepp, et al., 1990; Jones, et al., 1991; Sonnenberg, et al., 1991; Kurpakus, et al., 1991). The $\alpha_6\beta_4$ heterodimer has been localized to hemidesmosomes along the basal surfaces of the rat bladder carcinoma cell line 804G (Jones et al. *Cell Regulation* (1991); 2:427–438). These results suggested that integrins (e.g. $\alpha_6\beta_4$) may play an important role in the assembly and adhesive functions of hemidesmosomes.

Various prior art efforts have focused on purifying adhesion-facilitating proteins found in basement membrane. For example, Burgeson, et al., Patent Cooperation Treaty Application No. WO92/17498, disclose a protein which they call kalinin. Kalinin is said to facilitate cell adhesion to substrates; however, this material is apparently inactive with respect to hemidesmosome formation. See also, Marinkovich, et al., *J. Cell Biol.* (1992); 119:695–703 (k-laminin); Rouselie, et al., *J. Cell. Biol.* (1991); 114:567–576 (kalinin); and Marinkovich, et al., *J. Biol. Chem.* (1992); 267:17900–17906 (kalinin).

Similarly, a basement glycoprotein of about 600 kD made up of polypeptides in the range of 93.5 kD to 150 kD has been identified, and is known as GB3 or nicein. See, e.g., Verrando, et al., *Biochim. Biophys. Acta* (1988); 942:45–56; and Hsi, et al., *Placenta* (1987); 8:209–217. None of these materials have been effective in generating formation of hemidesmosomes, either in vitro or in vivo.

When cultured on tissue culture plastic in vitro, most epithelial cells do not assemble bona fide hemidesmosomes despite the fact that they appear to express all of the hemidesmosomal plaque and transmembrane components mentioned above. Indeed, it is only recently that cell lines such as 804G were discovered to have the ability to readily assemble hemidesmosomes in vitro under regular culture conditions (Riddelle, et al., 1991; Hieda, et al., 1992). Such cells are at last allowing detailed cell and biochemical analysis of the dynamics of hemidesmosome assembly.

For instance, it has been reported that substratum-associated staining by anti-hemidesmosome antibodies is greatly diminished in 804G cell cultures that enter in vitro wound sites (Riddelle et al., *J. Cell Sci.* (1992); 103:475–490). However, as closure of the wound became complete, anti-hemidesmosome staining along the substratum-attached surface was evident in the cells.

There are, however, many epithelial cells that do not attach to tissue culture dishes in a normal fashion, even after treatment with various growth factors. These cells do not produce normal hemidesmosomes or grow to resemble their in vivo phenotype. It would provide a tremendous advantage to have a system that was capable of maintaining epithelial cell growth in vitro wherein the cells maintained their normal phenotype.

SUMMARY

One embodiment of the present invention is a method for inducing hemidesmosome formation in epithelial cells in vitro. This method includes growing a first sample of epithelial cells under conditions that promote secretion of a hemidesmosome-formation facilitating cell matrix, wherein the first cells secrete the matrix; removing the first cells from the matrix, while leaving the matrix intact. The cell removal can be advantageously accomplished using $NH_4OH$. After removing the first cells, the method include growing a second sample of epithelial cells, preferably human epithelial cells of a different type in contact with the matrix whereby the second epithelial cells are induced to attach to the matrix and produce hemidesmosomes. In this method, the first epithelial cells can advantageously be 804G rat bladder carcinoma cells or, alternatively, NBTII rat bladder carcinoma cells.

A second embodiment of the present invention is a method for growing epithelial cells in vitro. In this method 804G rat bladder carcinoma cells are grown under conditions that promote the secretion of a cell matrix, wherein the 804G cells secrete the matrix. Following secretion of the matrix the 804G cells are removed from the matrix. Subsequently, the matrix is contacted with epithelial cells, wherein the contact promotes hemidesmosome formation in the epithelial cells. In this method the epithelial cells are preferably mammalian, and the mammalian cells are most preferably human. Even more advantageously, the epithelial cells are human skin cells.

Yet another embodiment of the present invention is an article of manufacture comprising a biocompatible shaped article adapted for use in vivo in a mammal, and a hemidesmosome formation-facilitating protein composition on the shaped article. Advantageously, the protein composition on the article is deposited by a tumor cell line of epithelial origin, preferably the rat carcinoma cell line 804G. Even more preferably, the protein composition contains at least one of the approximately 85 kD, 135 kD, 140 kD, 150 kD, or 400 kD proteins of the extracellular matrix deposited by the cell line 804G. Alternatively, the protein composition can be deposited on the article by the rat bladder cancer cell line NBTII.

Still another embodiment of the present invention is a composition for use in growing mammalian cells. This composition comprises the extracellular matrix protein of a mammalian cell, wherein the protein has the property of promoting hemidesmosome formation in cells contacting the protein, in a pharmaceutically acceptable carrier.

One additional embodiment of the present invention is the proteinaceous extracellular matrix proteins deposited by the cell line 804G, in substantially isolated form.

DETAILED DESCRIPTION

The present invention includes the discovery that certain cell lines produce an extracellular matrix that is capable of stimulating cellular adhesion and hemidesmosome assembly in other cells subsequently grown on the matrix. One such cell line is the bladder carcinoma cell line 804G. This cell line is described by Izumi, et al., *Cancer Res.* (1981); 41:405–409, and is maintained in permanent collection in the laboratory of inventor Jonathan C. R. Jones, from whom the cell line is readily available. This cell line is also available from Ryoichi Oyasu, Department of Pathology, Northwestern University Medical School, Chicago, Ill. The 804G cell line is also maintained as a Budapest Treaty patent deposit by the American Type Culture Collection, Rockville, Md., under accession number ATCC CRL 11555, made Feb. 24, 1994.

Ultrastructural data have been developed demonstrating that the 804G matrix is capable of inducing a number of cells to develop mature hemidesmosomes and attach to their growth substrate. Further, it has been discovered that the 804G matrix contains novel laminin-like molecules that participate in hemidesmosome assembly (unlike laminins and related molecules that have been purified in the prior art).

A novel matrix can now be prepared, produced by such cells as 804G cells, that can modulate the organization of hemidesmosomal antigens in unrelated cells maintained upon it. This effect appears specific to hemidesmosomal elements since adhesion plaque components do not obviously change their localization in cells maintained upon the matrix of the present invention.

To demonstrate this-new discovery, evidence is provided that the murine 804G matrix was capable of inducing assembly of "mature" hemidesmosomes in human epidermal carcinoma (SCC12) cells. It can be appreciated that it is uncommon to find compounds from murine cells that have such a profound effect on human tissue. In these experiments, described in more detail below, an increased number of hemidesmosome-like structures were found in SCC12 cells maintained upon the 804G matrix as compared to control experiments wherein SCC12 cells were grown on rat tail collagen. Moreover, the majority of these hemidesmosome-like structures in the 804G matrix grown cells were in contact with the cell substrate and possessed basal dense plates. The latter structures are often used of indicators as mature or formed hemidesmosomes (Krawczyk and Wilgram, 1973).

Although methods related to production and isolation of the 804G cell matrix are specifically disclosed, it can be appreciated that any cell matrix having the ability to support cell adhesion and hemidesmosome assembly is within the scope of the present invention. Matrices from other cell types, such as the murine bladder carcinoma cell line NBT II (ATCC CRL 1655) also appear to be able to induce attachment and hemidesmosome assembly in vitro. The NBTII cell line is also maintained as a Budapest Treaty patent deposit by the American Type Culture Collection, Rockville, Md., under accession number ATCC CRL 11556, made Feb. 24, 1994. It should be noted that the present specification the term "804G Matrix" is used to generically refer to any cell matrix with the ability to stimulate cell attachment and hemidesmosome formation.

One major use contemplated for the active components of the matrix of the present invention is in cell growth and attachment. A substrate upon which cells are to be grown is coated with the matrix or with purified hemidesmosome-promoting components thereof. The cells to be grown are then plated or applied to the substrate, and grown on the matrix. Such cells, including human cells in vitro and on vivo, will grow in an organized fashion on the substrate and will form hemidesmosomes. Hemidesmosome formation is a major advantage, because it greatly enhances the attachment of the cells to the substrate. Furthermore, it appears that the organization of cells growing on the matrix is significantly more advanced, more tissue-like, than cells grown without the matrix of the present invention.

The substrate used herein may be any desired substrate. For laboratory use, the substrate may be as simple as glass or plastic. For use in vivo, the substrate may be any biologically compatible material on which cells can grow. Suitable substrate materials may include shaped articles made of or coated with such materials as collagen; regenerated collagen; polylactic acid; biocompatible metals such as stainless steel and titanium; ceramic materials including prosthetic materials such as hydroxylapatite; synthetic polymers, including polyesters and nylons; and virtually any other material to which biological molecules can readily adhere.

A specific use of the present invention is for generating skin for allograft use. Epidermal cells, for example, are seeded onto a substrate of the present invention. These cells are grown on the substrate using conventional skin growth conditions, including nutrients and growth factors. The improvement of the present invention, that is, the use of the hemidesmosome-promoting matrix on the substrate, improves such ex vivo growth of skin over prior art techniques that do not use that matrix.

One particular use of the present invention is to increase epidermal cell adhesion to target surfaces. For instance, prostheses for dental implantation may be treated with the 804G matrix to stimulate periodontal cell attachment. Existing teeth may similarly be coated with the matrix as a treatment for gum (junctional epithelium) disease, such as gingivitis. Where a substrate is made of a natural or synthetic bioerodible material in the form of a sheet or fabric, such as woven or bonded collagen or polylactic acid, the matrix materials may be applied to the surface thereof or mixed in with the composition. Cells (such as epidermal cells) may then be grown on the matrix ex vivo to form transplantable or implantable materials; alternatively, the materials may be implanted and cells may be permitted to attach in vivo.

The 804G matrix will also be of great use in studies concerning hemidesmosome morphogenesis, $\alpha_6\beta_4$ integrin interactions with the extracellular matrix and for functional and structural analyses of new matrix components such as the laminin B2t-like rat molecule described below. Indeed, the 804G matrix may prove to be a tool that allows definition of hemidesmosome-mediated interactions between epithelial cells and the underlying connective tissues at the molecular level.

The 804G matrix of the present invention comprises four concanavalin-binding glycosylated proteins, of approximately 135 kD, 140 kD, 150 kD, and 400 kD, and a non-glycosylated, non-concanavalin protein of about 85 kD, all of which are recognized by polyclonal antibody raised against the 804G matrix. The methods of the present invention may be practiced with the complete, active matrix from 804G cells or a functionally equivalent matrix from other cells, and may also be practiced with any one of the individual protein components of the matrix which promotes hemidesmosome formation. (Such components can be empirically determined by isolating each component and testing it in accordance with the methods described herein.)

In addition to the active matrix and the active components thereof, the present invention also includes shaped articles coated with those materials. Preferably, those shaped articles are formed of materials other than glass, and include such forms as sheets, fabrics, prostheses, metal articles, bioerodible articles, and implantable articles.

Furthermore, pharmaceutical preparations of the active matrix or its active components are contemplated. These preparations can be in any suitable form, and generally comprise the active ingredient in combination with any of the well known pharmaceutically acceptable carriers. The matrix material may be harvested (as by scraping, abrading, or treatment with low concentrations of SDS) from surfaces on which appropriate matrix-depositing cells have been grown. Alternatively, the matrix materials may be prepared synthetically or through recombinant DNA techniques, or through purification of deposited matrix material. Those carriers can include injectable carriers, topical carriers, transdermal carriers, and the like. The preparation may advantageously be in a form for topical administration, such as an ointment, gel, cream, spray, dispersion, suspension, or paste. The preparations may further advantageously include preservatives, antibacterials, antifungals, antioxidants, osmotic agents, and similar materials in composition and quantity as is conventional. For assistance in formulating the compositions of the present invention, one may refer to Remington's Pharmaceutical Sciences, 15th Ed., Mack Publishing Co., Easton Pa. (1975), the relevant disclosure of which is hereby incorporated by reference.

Finally, epithelial cells of various types may be grown on the substrates or with the compositions contemplated herein.

Preparation of 804G Cell Matrix

To begin biochemical characterization of the matrix secreted by the 804G cells, we followed the procedure of Gospodarowicz (1984). Briefly, rat bladder carcinoma 804G cells were maintained at 37° C. in MEM with Earle's salts supplemented with 50 U/ml penicillin, 50 µg/ml streptomycin and 10% FCS (GIBCO LABORATORIES, Grand Island, N.Y.). This medium contains approximately 1.9 mM $Ca^{2+}$.

The 804G cells were grown to confluency on either plastic Petri dishes or glass coverslips. The culture medium was then discarded and the cells washed in sterile PBS. The cells were removed from their matrix by treatment for 5 minutes in sterile 20 mM $NH_4OH$, followed by three rapid washes with sterile distilled water.

The matrix was removed from the substrate by solubilization in 8M urea, 1% sodium dodecyl sulfate (SDS) in 10 mM Tris, pH6.8. The 804G matrix polypeptide profile was analyzed by Sodium Dodecylsulfate Polyacrylamide Gel Electrophoresis (SDS-PAGE) using routine experimental methods known to those with skill in the art.

A preparation having approximately 20 µg of the solubilized 804G cell matrix was loaded onto an acrylamide gel and electrophoresed. As a control, an extract from the removed 804G cells, having approximately 20 µg per lane, was also loaded onto the acrylamide gel. Following gel electrophoresis we noted that there were three major polypeptides in the matrix preparation ranging in molecular weight from 150–135 kD. A minor polypeptide of 85 kD was also present in the matrix preparation. After PAGE, the separated polypeptides were transferred to nitrocellulose by standard well known methods. Amido black stains of the dyed protein samples were transferred to the nitrocellulose indicating a successful completion of the Western Blotting procedure.

Concanavalin Binding to 804G Matrix

A strip of the Western Blot nitrocellulose containing separated matrix proteins was incubated with Concanavalin A. Non-specific protein binding to the matrix molecules was blocked by first incubating the strip for 30 minutes at room temperature with 2% (w/v) polyvinylpyrrolidone in PBS. Concanavalin A was added to the blocking buffer and the filter was then incubated with gentle shaking at room temperature. Horse radish peroxidase (HRP) was added to visualize Concanavalin A binding.

Four matrix polypeptides of 135, 140, 150 and 400 kD were recognized by Concanavalin A. As is known in the art Concanavalin A binding indicates that these matrix components are glycosylated. To identify proteins on the Western Blot that were specific to the matrix, we raised polyclonal and monoclonal antibodies.

Production of Polyclonal Antibodies Against the 804G Matrix

Antiserum was prepared by injecting urea/SDS solubilized 804G cell matrix, as described above, into a rabbit by standard methods. Briefly, solubilized 804G matrix was mixed with Freund's adjuvant and injected into a rabbit. Serum was collected at three weekly intervals following one booster injection as detailed by Harlow and Lane (1988).

The isolated polyclonal antiserum (J18) had antibodies recognizing the four 135–400 kD species that bound concanavalin A, as well as an 85 kD polypeptide. Therefore, their appears to be a non-glycosylated 85 kD species in the matrix along with four additional glycosylated polypeptides.

Following our experiments with the polyclonal antibodies, we produced monoclonal antibodies specific for the 804G matrix by the following method.

Production of Monoclonal Antibodies Against the 804G Matrix

A mouse monoclonal IgG (5C5) against the 804G cell matrix was prepared by injecting a solubilized 804G cell matrix sample into several mice. At two and three weeks after the initial injection the mice were boosted with further 804G matrix injections. Five days following the final boost their spleens were removed and isolated spleen cells were fused with the myeloma cell line Sp2 for the production of hybridomas using standard techniques (Galfre and Milstein, 1981). Hybridoea cells producing antibody against matrix elements were selected on the basis of their immunoblotting and immunofluorescence reactivities against matrix samples. Selected hybridoma cells were cloned twice by limited cell dilution as described in Harlow and Lane, 1988.

Western Blots with one of the mouse monoclonal IgG antibodies (5C5) recognized only a 150 kD and a 140 kD polypeptide in the matrix preparation. Antibody 5C5 and the J18 serum were then used in immunoprecipitation studies to investigate potential protein-protein interactions in the matrix.

Immunoprecipitation Studies of the Matrix

Immunoprecipitation of the 804G matrix was performed using conventional methodology. In brief, the 804G matrix was treated with RIPA buffer (0.1M Tris-HCl, pH 7.2, containing 0.15M NaCl, 1% Triton X100, 0.1% SDS, 1% Na deoxycholate, 10 mM EDTA, 1 mM phenylmethylsulfonyl fluoride), clarified by centrifugation, and incubated with either the rabbit serum J18 or monoclonal antibody 5C5. The resulting antibody-antigen complexes were immunoprecipitated with *Staphylococcus aureus* Protein A by methods known to those with skill in the art.

The immunoprecipitated molecules were separated by SDS-PAGE and transferred to a Western blot by the methods described in more detail above. Lanes 1 and 2 from the gel were immunoblotted with either goat anti-rabbit, or goat anti-mouse antibodies, conjugated to HRP for visualization.

The polyclonal J18 antibodies recognized similar sets of polypeptides in both the matrix and 5C5 immunoprecipitate. Major protein bands were found in both samples at 150, 140 and 135 kD. This result indicated that the J18 serum contained antibodies against all of the major proteins of the matrix.

5C5 antibodies recognized primarily 150 kD and 135 kD polypeptides in both the 804G matrix and 135 kD immunoprecipitate. The 5C5 antibodies apparently precipitated all of the molecular species in the matrix that were recognized by the J18 serum antibodies. In contrast, the 5C5 antibodies recognized only the 150 and 135 kD polypeptides in both the matrix preparation and the J18 serum immunoprecipitate. As the 5C5 antibodies were able to precipitate most of the matrix proteins, yet only identified two proteins on a denaturing gel, we believe that the major proteins interact and are associated with one another in their normal state. Thus, these two major 804G matrix proteins are believed to be constructed of subunits comprising the various proteins identified above.

To investigate the protein composition of the 804G matrix, we probed a Western Blot of solubilized matrix proteins with polyclonal serum against the 400 kD and 200 kD chains of Engelbreth-Holm-Swarm (EHS) laminin.

Western Blot of Matrix Proteins Probed with Anti-laminin Antibodies

Polyclonal antibodies against the 400 kD and 200 kD chains of EHS laminin were purchased from Collaborative Research Incorporated (Bedford, Mass.). A preparation of laminin (approximately 10 μg per lane) and a preparation of the solubilized 804G cell matrix (approximately 20 μg per lane) were denatured and run on a SDS gel, then subsequently transferred to nitrocellulose. We noted that the amido black stain used on the proteins run in lanes 1 and 2 was transferred to the nitrocellulose filter indicating that the blotting was successful.

Incubation with the HRP conjugated anti-laminin polyclonal antibodies resulted in a strong reactivity in the laminin lanes, but there was very little detectable reactivity between the laminin polyclonal antibodies and the 804G cell matrix preparation. In a related experiment, the Western Blot was immunoblotted with labeled samples of either rabbit polyclonal anti-804G serum J18 or the monoclonal antibody 5C5, respectively. These antibodies failed to recognize any laminin polypeptides, although they did recognize polypeptides in the matrix preparation as expected from previous experiments described above.

It appeared that there was little antibody cross-reactivity between laminin and the 804G matrix. For this reason, we attempted to isolate genes expressing polypeptides reactive with the J18 anti-804G antibodies.

Isolation of Clones Corresponding to Matrix Polypeptides

A human keratinocyte lambda gtll expression library was purchased from Clontech Labs., Inc., Palo Alto, Calif. and screened with the 804G matrix polyclonal serum J18 according to Huynh, et al., (1985). Antibodies absorbed by the fusion protein products of these three clones showed reactivity with both 140 kD and 85 kD molecular weight species in an 804G matrix preparation and a whole cell extract of SCC12 cells.

To further characterize positive clones, plaque lifts of nitrocellulose-bound fusion proteins were used to epitope select antibodies (Sambrook, et al., 1989). cDNA inserts were subcloned into M13 vectors and sequenced by the Sanger dideoxychain termination method (Sanger, et al., 1977). Sequence analyses were made using the GCG sequence analysis software package (University of Wisconsin Biotechnology Center, Madison, Wis.).

The nucleotide sequence of these clones revealed that they encode a region spanning amino acids 550–810 in domain I/II of a recently identified variant of the B2 chain of laminin that has been termed laminin B2t (Kallunki, et al., 1992). The B2t variant is not contained in EHS laminin, and therefore represents a new subunit. This experiment illustrates the cross-reactivity of the matrix associated polypeptides with the laminin B2t variant.

Following this experiment we attempted to ascertain the location of 804G matrix polypeptides in intact tissue samples.

Immunofluorescence Localization of 804G Matrix Antigens in Intact Tissue 804G cells were processed for immunofluorescence using the 5C5 monoclonal and J18 polyclonal antibodies. Initially, the 804G cells were fixed and extracted for 2–3 min in 20° C. acetone prior to antibody incubation. Double labeling was carried out as detailed below.

Cells on coverslips were first incubated in a mixture of primary antibodies for 1 hr at 37° C. The coverslips were extensively washed in PBS and then overlaid with the appropriate mixture of rhodamine and fluorescein conjugated secondary antibodies by well known methods. Processed tissues were viewed on a Zeiss Photomicroscope III fitted with epifluorescence optics while cultured cells were viewed on a Zeiss laser scan microscope (LSM10) equipped with Argon and HeNe lasers for dual fluorescence confocal imaging (Carl Zeiss, Thornwood, N.Y.). As controls for the immunofluorescence analysis, cells were incubated in normal mouse, rat or rabbit IgG as well as secondary antibodies alone in order to assess staining due to non-specific antibody binding.

Both the J18 serum, 5C5 antibodies and the antibodies selected from the J18 serum using the laminin B2t fusion proteins were localized in cryo-sections of rat epithelial tissues by immunofluorescence microscopy. All of these antibody preparations show intense staining along the region of epithelial-connective tissue interaction.

All of the above experiments have been related to the structure and function of the 804G matrix. Thus far, we have determined that the 804G matrix peptides immunologically related to the B2t laminin variant, and that antibodies directed against matrix proteins have been found at the epithelial-connective tissue juncture.

One important aspect of the present invention is our discovery that the 804G matrix, described in detail above, can unexpectedly provide a substrate capable of stimulating epithelial cell growth in vitro. We discovered that epithelial cells grown on the 804G matrix produced hemidesmosomes, as expected from normal cells exhibiting an in vivo morphology. To illustrate this aspect of the invention, we performed the following experiments. Initially, we grew the SCC12 human tumor cell line on the 804G matrix to determine its potential for normal growth in vitro.

Functional Analyses of Epithelial Cells Grown on the 804G Matrix

Antibodies against a 230 kD plaque component of the hemidesmosome have been detailed before (Klatte et al., 1989). Monoclonal and polyclonal antibodies directed against the cytoplasmic domain (N-terminus) of a 180 kD type II membrane element of the hemidesmosome have been described in Hopkinson et al., (1992) and Riddelle et al. (1992). An antibody against the $\beta_4$ integrin subunit was purchased from Telios (San Diego, Calif.).

SCC12 cells were maintained on the 804G cell matrix for 24 hrs to assess the impact of the matrix on hemidesmosome protein localization in a tumor cell line that, under normal circumstances, does not assemble bona fide hemidesmosomes in vitro. We chose to complete our studies in 24 hrs to minimize matrix degradation and/or modification by the added cells, a possibility that Carter, et al. (1990) have discussed. Each experiment was repeated at least four times involving the analysis of more than 500 cells. As controls, the SCC12 were plated onto other matrices, such as glass and rat tail collagen. After 24 hrs the cells were processed for indirect immunofluorescence using antibodies directed against the 230 kD, 180 kD and $\alpha_6\beta_4$ integrin components of the hemidesmosome, double labelled with antibodies against the 804G cell matrix.

Cells on coverslips were first incubated in a mixture of primary antibodies for one hour at 37° C. The coverslips were extensively washed in PBS and then overlaid with the appropriate mixture of rhodamine and fluorescein conjugated secondary antibodies. Processed tissues were viewed on a Zeiss Photomicroscope III fitted with epifluorescence optics. As controls, cells were incubated with normal mouse, rat or rabbit IgG as well as secondary antibodies alone to assess staining due to non-specific background.

In SCC12 cells maintained for 24 hrs on glass and rat tail collagen, the 230 kD, 180 kD, $\alpha_6\beta_4$ integrin subunits localized to the periphery of the cells along their substratum attached surfaces. The staining sometimes resembled a fuzzy band surrounding the cell periphery, or linear streaks near the cell edges (see also Hopkinson, et al., 1991). Anti-matrix antibodies in the J18 serum generated a diffuse staining along the region of cell-substrate interaction in cells maintained on rat tail collagen, with no obvious correlation to the staining generated by the hemidesmosomal antibody probes. The reactivity of J18 antibodies with the SCC12 cells by immunofluorescence is consistent with the positive immunoblotting reactivity using antibodies selected from the J18 serum by the human laminin B2t fusion proteins. Since antibodies in the J18 serum failed to recognize rat tail collagen alone, our results provide some indication concerning the matrix that the SCC12 cells themselves secrete.

In SCC12 cells maintained on the 804G cell matrix, the 230 kD, 180 kD and $\alpha_6\beta_4$ integrins show a dramatically different pattern of distribution compared with that observed in cells maintained on rat tail collagen or glass. The patterns that these hemidesmosomal antibodies generate are similar to that seen in 804G cells processed for immunofluorescence using the same antibodies, as described above. Furthermore, this staining, in most instances, appears coincident with those patterns generated by antibodies in the whole J18 serum.

In addition, 5C5 antibodies or those J18 antibodies epitope selected from the laminin B2t fusion proteins were also localized in SCC12 cells maintained on the 804G matrix. The distribution of these antibodies compared with that of the 230 kD hemidesmosomal plaque component. It should be noted that the 230 kD antigen distribution in the SCC12 cells mirrors that of the staining generated by the 5C5 and epitope selected antibodies.

Immunoblotting analyses were undertaken to examine whether there was a change in the amounts of both the 230 kD and 180 kD hemidesmosomal components in SCC12 cells maintained on 804G cell matrix for 24 hrs compared to SCC12 cells maintained for the same length of time on other matrices. There was no apparent difference in the quantity of both the 230 kD and 180 kD polypeptides in SCC12 cells maintained on the various matrices as assessed by this procedure.

In contrast to hemidesmosomal components, the $\alpha_5\beta_1$ integrin complex, a component of the microfilament associated-adhesion plaque (Burridge, et al. 1988), localize primarily at the peripheral cell-substratum associated surface of SCC12 cells regardless of whether it is maintained on rat tail collagen or the 804G cell matrix.

Our studies of epithelial cell growth on the 804G matrix were not confined to SCC12 cells. Normal Human Keratinocytes (derived from human foreskins), HaCaT (immortalized cells), and SCC13 cells also exhibited almost identical responses when grown on the 804G matrix in comparison to the SCC12 cells discussed above. In each of these cell types, growth on the 804G matrix led to a redistribution of integrins and mature hemidesmosome formation.

In addition, experiments similar to those described above have been performed on the matrix produced by the NBTII cell line. The results from these experiments are virtually identical to those illustrated for the 804G matrix. Cells grown on the NBTII matrix were stimulated to form mature hemidesmosomes and redistribute intracellular integrins.

To further investigate the effect of growing epithelial cells on the 804G matrix, we examined SCC12 cells under the electron microscope.

Electron Microscopic Examination of the Impact of the 804G Cell Matrix on Hemidesmosome Assembly in 8CC12 Cells SCC12 cells were fixed and processed for electron microscopy as described elsewhere (Riddelle, et al., 1991). Thin sections of cells were made perpendicular to their substrate, placed on 300 mesh electron microscope grids (Tousimis Corp., Rockville, Md.), stained and then viewed at 60 kV in a JEOL 100CX electron microscope.

SCC12 cells maintained for 24 hrs on either rat tail collagen or the 804G matrix were examined by conventional electron microscopy. This procedure involved analyzing thin sections of the SCC12 cells cut perpendicularly to their substrate at intervals of 10 microns through a population of cells. By assessing sections at this distance apart we avoided the possibility of observing the same hemidesmosome more than once.

In SCC12 cells maintained for 24 hrs on rat tail collagen, hemidesmosome-like structures were observed towards the cell periphery. In 17 SCC12 cells incubated on rat tail collagen we observed 9 hemidesmosome-like structures, none of which possessed a basal dense plate. This count was made over a distance of 306 microns (i.e. 1 hemidesmosome-like structure/34 microns of the ventral surfaces of SCC12 cells). The close apposition of three hemidesmosome-like structures was seen in one micrograph, however, this was highly unusual. In many basal profiles of SCC12 cells on rat tail collagen no hemidesmosomes were observed.

In contrast, 103 hemidesmosome-like structures, of which 92 possessed basal dense plates, were observed in cross sectional profiles of SCC12 cells incubated on the 804G matrix. These observations were made over a distance of 504 microns (i.e., 1 hemidesmosome-like structure/4.9 microns of SCC12 ventral surface). Unlike the "rudimentary" hemidesmosomes seen on cells incubated with rat tail collagen, these hemidesmosome-like structures were not confined to the periphery of the cell, but also were found underlying the nucleus. These SCC12 cells also appeared to possess tufts of intermediate filaments associated with their cytoplasmic face.

In addition to electron microscopy of SCC12 cells, we looked for hemidesmosome assembly in Human Keratinocytes, HaCaT cells, and SCC13 cells. As reported above in relation to immunofluorescence experiments, each of these other mammalian epithelial cells began redistributing integrins and forming mature hemidesmosomes. Our electron microscope studies revealed significant similarities in the affect of the 804G matrix on SCC12 cells, Human Keratinocytes, HaCaT cells, and SCC13 cells.

To demonstrate that the 804G cell matrix could retain its ability to induce changes in epithelial cells after solubilization, we coated glass coverslips with solubilized matrix elements.

Photolithography with 8046 Matrix Elements

To determine whether an isolated matrix sample could retain its ability to induce changes in hemidesmosomal and integrin localization 804G cells were grown and removed from their matrix as described above. A mild SDS buffer (RIPA) was used to solubilize and remove the matrix from its growth substrate. Following solubilization in RIPA buffer, the matrix elements were dialyzed extensively against phosphate buffered saline and then coated in a microscopic pattern onto glass coverslips using a photolithographic technique described by Hockberger et al. (*Journal of Neuroscience* (1988) 8(11):4098–4120).

Briefly, a clean coverslip was first spin-coated with "photoresist". A mask was placed on top of the photoresist layer followed by illumination with UVlight. At all of the points not covered by the mask the photoresist was UV cross-linked to the glass coverslip. Dialyzed 804G matrix elements were then added to the coverslip and bound along the entire surface of the coverslip. The photoresist and its bound matrix elements were removed from the non-UV linked areas of the coverslip by acetone treatment. A defined pattern of 804G matrix elements, configured as the inverse of the mask, was retained for further examination.

In immunofluorescence studies using our matrix polyclonal antiserum, we demonstrated that SCC12 cells grown on these coverslips form hemidesmosomes in formations corresponding to the deposited pattern of 804G elements. Remarkably, the location of $\beta_4$ integrins on SCC12 cells grown on these coverslips also followed the deposited matrix patterns. This indicated that the matrix maintained its functionality following mild SDS denaturation and deposit onto a solid substrate. By following this protocol, other solid substrates could be coated with the 804G matrix to stimulate hemidesmosomal formation in epithelial cells.

Thus, we have demonstrated that the 804G cell matrix is able to induce attachment and hemidesmosome assembly in many types of mammalian cells.

It should be noted that the present invention is not limited to only those embodiments described in the Detailed Description. Any embodiment which retains the spirit of the present invention should be considered to be within its scope. However, the invention is only limited by the scope of the following claims.

I claim:

1. A method for inducing hemidesmosome formation in epithelial cells in vitro, comprising:
   growing 804G rat bladder carcinoma cells or NBTII rat bladder carcinoma cells under conditions that promote the secretion of a hemidesmosome-formation facilitating cell matrix, wherein said 804G or NBTII cells secrete said matrix;

separating said 804G or NBTII cells from said matrix, while leaving said matrix intact; and growing epithelial cells in contact with said matrix whereby said epithelial cells are induced to attach to the matrix and produce hemidesmosomes.

2. The method of claim 1, wherein said epithelial cells are human.

3. The method of claim 1 wherein said epithelial cells are human skin cells.

4. The method of claim 1, wherein said matrix is secreted by said 804G cells.

5. The method of claim 1, wherein said matrix is secreted by said NBTII cells.

6. The method of claim 1, wherein said separating comprises washing said 804G or NBTII cells in $NH_4OH$.

7. A method for growing epithelial cells in vitro comprising:

growing 804G rat bladder carcinoma cells under conditions that promote the secretion of a cell matrix, wherein said 804G cells secrete said matrix;

separating said 804G cells from said matrix;

contacting said matrix with epithelial cells, wherein said contact promotes hemidesmosome formation in said epithelial cells; and allowing said epithelial cells to grow in the presence of said matrix.

8. The method of claim 7 wherein said epithelial cells are mammalian.

9. The method of claim 8 wherein said mammalian cells are human.

10. The method of claim 7, further comprising the step of solubilizing said matrix prior to said contacting step.

11. The method of claim 10, further comprising introducing the grown epithelial cells in vivo.

12. The method of claim 7, further comprising the step of applying said matrix to a shaped article prior to said contacting step.

13. The method of claim 12, wherein said shaped article may be used in vivo.

14. In a method for growing mammalian epithelial cells on a shaped article, wherein the improvement comrpises providing on said shaped article a hemidesmosome-inducing extracellular matrix obtainable from 804G or NBTII rat bladder carcinoma cells prior to grwoing said epithelial cells on said article.

15. The method of claim 14, wherein said shaped article is an implantable prosthesis.

16. The method of claim 14, wherein said shaped article is a dental prosthesis.

17. The method of claim 14, wherein said shaped article is in the form of a sheet or a fabric.

18. The method of claim 14, wherein said Epithelial cells are human.

19. The method of claim 18, wherein said shaped article is introduced in vivo.

20. The method of claim 18, wherein said shaped article is an implantable prosthesis.

21. The method of claim 18, wherein said shaped article is a dental prosthesis.

22. The method of claim 18, wherein said shaped article is in the form of a sheet or a fabric.

23. The method of claim 14, further comprising introducing the grown epithelial cells in vivo.

* * * * *